United States Patent [19]

Törnblom

[11] Patent Number: 4,837,510

[45] Date of Patent: Jun. 6, 1989

[54] DEVICE FOR SUPPRESSION AND/OR SEPARATION OF SIGNALS DUE TO MAGNETIC OXIDE SCALES IN HOT CAST BILLETS

[75] Inventor: Bengt H. Törnblom, Västeras, Sweden

[73] Assignee: Tornbloms Kvalitetskontroll AB, Sweden

[21] Appl. No.: 146,175

[22] Filed: Jan. 20, 1988

[30] Foreign Application Priority Data

Jan. 30, 1987 [SE] Sweden .................. 8700359

[51] Int. Cl.$^4$ .................. G01N 27/72; G01R 33/12
[52] U.S. Cl. .................. 324/225; 324/232; 324/239
[58] Field of Search .................. 324/225, 232, 236–243, 324/227

[56] References Cited

U.S. PATENT DOCUMENTS 4,274,054  6/1981  Savidge et al. .................. 324/225

Primary Examiner—Reinhard J. Eisenzopf
Assistant Examiner—Walter E. Snow
Attorney, Agent, or Firm—Watson, Cole Grindle & Watson

[57] ABSTRACT

Defect detecting equipment includes a device which detects the presence of, for example, disturbing magnetic material such as cold oxide scales in a test object, in order thus to control, for example, that disturbances of a magnetic origin are not confused with surface cracks without being discovered. By utilizing eddy current techniques, phenomena which are harmless to the process can be separated from dangerous surface cracks, thus avoiding the scrapping of crack-free test objects. The invention is based on signal-processing at least two signals, for example H1 and L1, originating from a test object sensing tansducer, by means of a vector transformation method, and distinguished between harmful and harmless phenomena (e.g. cracks and oxide scales) as a function of a comparison of signals, S1 and S2, from at least two transformation blocks.

13 Claims, 5 Drawing Sheets

DEVICE FOR SUPPRESSION AND/OR SEPARATION OF SIGNALS DUE TO MAGNETIC OXIDE SCALES IN HOT CAST BILLETS

TECHNICAL FIELD

This invention relates to the field of the control and/or supervision of defects in bulk material, for example the detection of cracks using eddy current techniques in hot continuously cast steel ingots and the like. The invention can be considered to be an improvement in the subject-matter disclosed in Törnblom's U.S. patent application 085,173 filed on Aug. 14, 1987.

DISCUSSION OF PRIOR ART

In conventional defect (or crack) detection, a vector transformation technique is employed using a transformation unit, the aim being to combine and sum up different detected analog signals, after the signals have been weighted and provided with polarity constants etc., such that desired signals (i.e. those representing defects that need to be detected) are emphasized whereas undesired signals are suppressed in the resultant analog output signal from the transformation unit. However, in those cases where it is desired to suppress, for example, signals caused by oxide scale deposits on an ingot, the suppression does not function other than for a limited number of types of oxide scale deposit. The reason for this is that deposits of oxide may vary greatly in size, shape, orientation, and so on. In other words, the transformation is only effective for those oxide scales which correspond to the current setting of the transformation unit. This is an obvious drawback which is difficult to overcome with conventional vector transformation techniques.

The present invention shows how, in a relatively simple manner, simple conventional transformation units can be supplemented with a comparison unit, which by means of special signal processing is able to distinguish between an important defect or crack signal or an unimportant oxide scale signal. It should then be noted that the unwanted signals, in this case the oxide scale signals, need not be greatly suppressed but that the comparison is determining for the classification of the type of signal. Since the principle is general by nature, it can also be employed for suppression/separation of other signal-generating phenomena in addition to oxide scales. However, eliminating spurious defect detection caused by oxide scales is valuable, since these scales are indefinite in size and shape and thus—at the same time—difficult to suppress using conventional vector transformation techniques. The following description is therefore to be considered one of many feasible examples of how the present invention can be applied and utilized.

The invention may, for example, be regarded as an important reliability-improving complement to crack detection equipment using eddy current techniques, which warns of the presence of disturbing magnetic material, for example of the oxide scale type, on otherwise substantially non-magnetic test objects.

The fact that the permeability $\mu_r$ of a localised region on a test object gives rise to disturbing vectors of varying magnitude, when $\mu_r > 1$, has long been a wellknown problem in the eddy current testing of non-magnetic material. Heretofore, various attempts have been made to remove the magnetic material, for example, magnetic oxide scales and the like, for example by flushing the surface of a hot billet with water under high pressure, but these removal techniques are expensive and time-consuming and sometimes unreliable.

As far as the applicant knows, the existing specialist literature does not describe any method or device corresponding to what is described herein. The basic idea behind the invention is to first detect the presence of magnetic material and then to alert and control the defect detection process.

By using a simple transformation unit one variable can be suppressed per unit. However, if required complex hierarchic networks can then be built up with these simple transformation units, so that the resultant output signal obtained is not influenced by any of the suppressed signals, an arrangement which is felt to be unique to the invention.

The primary object of the invention is to detect the appearance of magnetic material and to warn of its presence and effects in order thus to be able to prevent the magnetic disturbances being confused with actual cracks. It would, of course, be possible to measure the surface temperature of the billet via, for example, one or more radiation pyrometers, thereby determining whether colder surface areas exist and whether the material is magnetic or not. However, for reasons which are easily understood, this method suffers from numerous and considerable drawbacks.

The invention enables, for example, the combination of facilities for the detection of cracks and the detection of magnetic material by using, for example, a single eddy current transducer. Also, certain parts of the electronic measuring equipment associated with the transducer may also be common to both facilities. This involves advantages both from the point of view of economy and from the point of view of measuring technique.

In eddy current testing, for example crack detection, on non-magnetic material, it is usually assumed that no magnetic permeability is present in the material, i.e. that the test object is totally non-magnetic.

In all the above cases it may occur that foreign magnetic particles and the like occur in or on the material, or that, for example, a certain limited region on a hot billet surface has become magnetic in spots because of a partially low surface temperature.

In a continuous casting process, the temperature of the cast strand may vary as a result of different process parameters, which are changed while casting is in progress. In this case, also the billet surface is often coated with larger or smaller so-called oxide scales, the Curie temperature of which is often somewhat lower than that of the actual steel. Still it happens that the oxide scales, which contain FeO, $Fe_2O_3$ and $Fe_3O_4$, because of insufficient mechanical contact with the surface of the billet, sometimes attain a temperature below their Curie temperature, whereby they become magnetic and greatly disturb the eddy current testing.

In this context it is important to realise that irrespective of the reason for the occurrence of magnetic material in or on the test object, its occurrence is invariably disturbing to an eddy current testing technique adapted to non-magnetic test objects, and that this is particularly true in the case of so-called multi-frequency testing.

The present invention aims to provide a solution to the above-mentioned problems and other problems associated therewith.

SUMMARY OF THE INVENTION

According to the invention there is provided a device for monitoring a test object for the presence of a selected phenomenon, which device comprises at least one sensor generating an output-signal means to move the sensor relative to the test object, and means to process the output signal originating from the movement of the sensor relative to the test object to detect the presence of the selected phenomenon, which is characterized in that the effect on the output signal of a second phenomenon is suppressed relative to the effect on the output signal of the selected phenomenon by the processing means operating selectively on the said output signal.

The invention may be regarded as an important complement to the following Swedish patent applications and patents: Nos. 7507857-6, 8601785-2, 8603113-5 and 8603240-6 and U.S. Pat. No. 4,237,419 British patent No. 2041535, U.S. patent application No. 926850 (filed Nov. 3rd, 1986), U.S. Pat. No. 4,646,013, U.S. Pat. No. 4,661,777 and U.S. patent application No. 702,314 (filed Feb. 15th, 1985). The terminology and the drawings of these patents/applications are applicable, in parts, to the present invention as well. Since the majority of the patents/applications mentioned above include the detection of cracks on hot non-magnetic material, magnetic disturbances ca be expected, which justifies a complement according to the present invention.

Definitions of Terms Used

In this specification the following definitions apply:

The term EDDY CURRENT TESTING includes control and/or measurement based on the use of frequencies and/or frequency components within a range extending from a few Hz to several MHz.

The term FREQUENCY includes CARRIER FREQUENCY, i.e. the frequency with which a transducer/-sensor is supplied with electrical power and also embraces a frequency component.

The term TEST OBJECT includes a continuously cast billet, a rod, a tube, a sheet or a volume of liquid molten steel and also embraces particles and objects on the surface of the test object, for example oxide scales and the like.

The term TRANSDUCER/SENSOR includes a surface transducer coil supplied with current, which coil moves, for example, in planes parallel to the surface, or part of the surface, of a test object.

The term LIFT-OFF (LO) means the distance of a transducer/sensor relative to the surface of a test object.

The term MAGNETIC material means that the material is influenced by a permanent magnet, i.e. that the relative permeability ($\mu_r$) is greater than unity.

The term FAULT VECTOR (FV) means that vector which arises in the impedance plane of the transducer/-sensor when the transducer/sensor moves over a defect.

The term $\mu$-VECTOR ($\mu V$) means that vector which is caused by the influence of magnetic material on the transducer/sensor.

The term VECTOR LOBE (VL) means that surface in the impedance plane within which fault vectors are situated.

The term NON-MAGNETIC MATERIAL means, for example, steel ingots such as slabs, billets and the like, the temperature of which at the time of measuring lies above the so-called Curie temperature or Curie point. It may also be a magnetic steel pipe which, by way of saturation magnetization in conventional manner, has received an apparent permeability substantially corresponding to $\mu_o$.

It should be pointed out that the following description assumes that the reader has a certain basic knowledge of impedance diagrams, etc., and therefore the more elementary bases and details have been omitted in order to keep the description to acceptable lengths. For the same reason an application of the invention will be described in which the device is based on eddy current technique. However, it should be appreciated that other techniques, for example leakage fluxes, as well as the use of sensors of the Hall element type, and so on, are embraced by the invention and the following description should be read with that fact in mind.

BRIEF DESCRIPTION OF THE DRAWINGS

The invention will now be described in greater detail, by way of example, with reference to the accompanying drawings, wherein.

DESCRIPTION OF PREFERRED EMBODIMENTS

Figure 1:
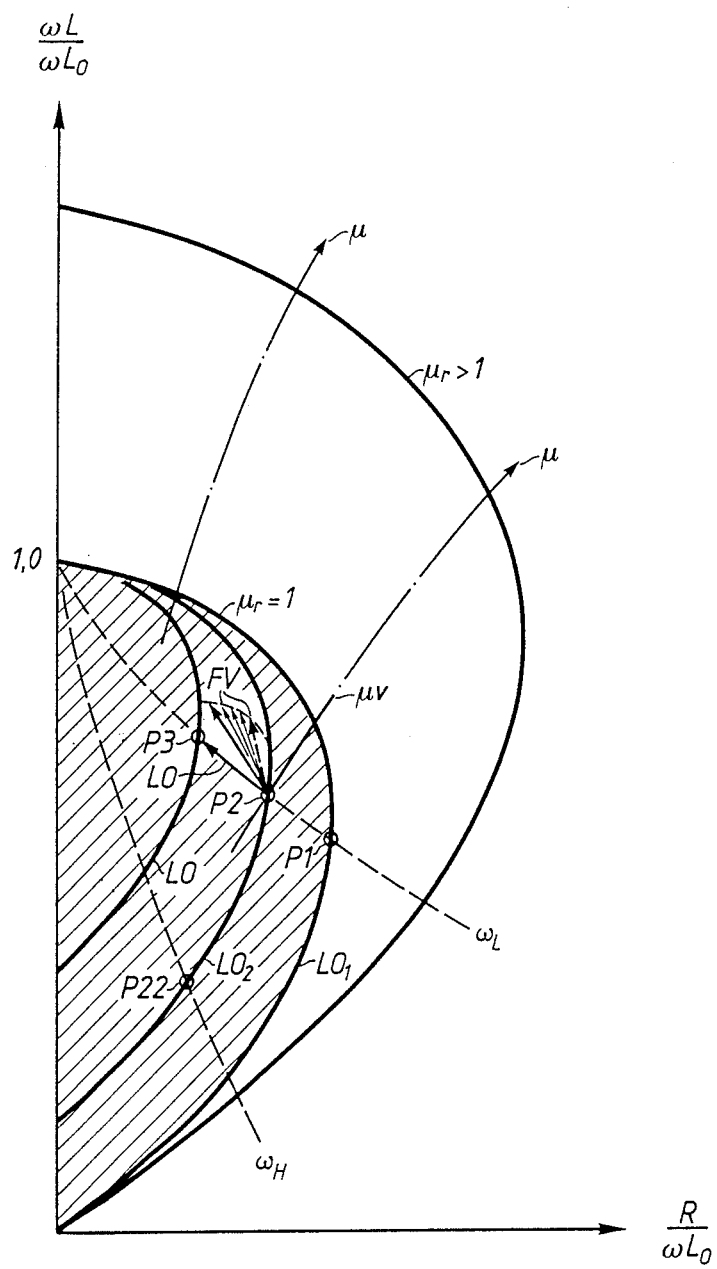
FIG. 1 shows a normalized impedance diagram for a conventional transducer.

FIG. 1 shows a normalized impedance diagram, of conventional character, for a transducer/sensor. U.S. Pat. No. 4,646,013 (Törnblom) shows in FIG. 3 a corresponding impedance diagram in the case of a test object of non-magnetic material, i.e. the impedance curves are based on $\omega L/\omega L_0 = 1.0$. In the accompanying FIG. 1, however, the impedance plane has been supplemented with curves for a magnetic material, in other words, $\mu_r < 1$. As will be clear, the permeability, $\mu$, has an amplification effect on the electric impedance, which may greatly disturb the eddy current measurement of cracks and the like defects, especially when the cracks have an elongate direction in the impedance plane which largely coincides with the $\mu$-direction. The direction of the magnetic permeability in the impedance plane is clear from the $\mu$-vectors shown by the dot-dashed lines displayed on the graph of FIG. 1.

In, for example, crack detection on hot (>780° C.) steel ingots, the temperature of which exceeds the Curie temperature, the steel is non-magnetic. If a simple surface transducer is used for crack detection and the distance of the transducer to the billet surface varies, for example between $LO_2$ and $LO_3$, the impedance of the transducer will also vary. This impedance variation has different magnitudes at different carrier frequencies, and for a certain frequency, $\omega_L$ in FIG. 1, it is shown as a vector LO between points P2 and P3. Depending on the direction of the LO-movement, this vector may reverse its direction, that is, it may change polarity.

The $LO_1$-curve in FIG. 1 represents the case where there is strong inductive coupling between the transducer and the test object, for example coupling such as would occur when LO=0 (i.e. the transducer is in contact with the surface). It is also possible, for example, to define the $LO_1$-curve as the smallest LO-distance which is possible in practice. For the non-magnetic material, this means that the impedance curves are contained within the sectioned part of FIG. 1.

Now, let it be assumed that the transducer is at a distance $L0_2$ from the surface of the test object and that the transducer is powered with a carrier frequency $\omega_L$, which means that operation is occurring at point P2 in FIG. 1. When the transducer is positioned over a crack, a so-called fault vector (FV) is obtained, the direction of which lies near the LO-direction, which is described in detail in the above-mentioned U.S. Pat. No. 4,646,013. Now, if the test object for some reason should become magnetic, i.e. $\mu_r > 1$, a vector would be obtained in a corresponding manner, which in FIG. 1 is shown as a vector $\mu V$. It should be pointed out that the vectors FV and $\mu V$ after detection have different signal frequency contents, i.e. different duration, which is due to the fact that the crack has an appearance which is different from (shorter than, for example) the magnetic region on the test object, which may be an increased thickness of oxide scale. These vectors have, for two different carrier frequencies, $\omega_L$ and $\omega_H$, been separated from FIG. 1 and are plotted graphically in FIGS. 2 and 3. These vectors can be conventionally transformed into, for example, voltages which may be rectified via, for example, phase-controlled rectifiers. In this way, it is possible to separate vectors having different directions, i.e. different phase positions, in the impedance diagram.

Figure 2:
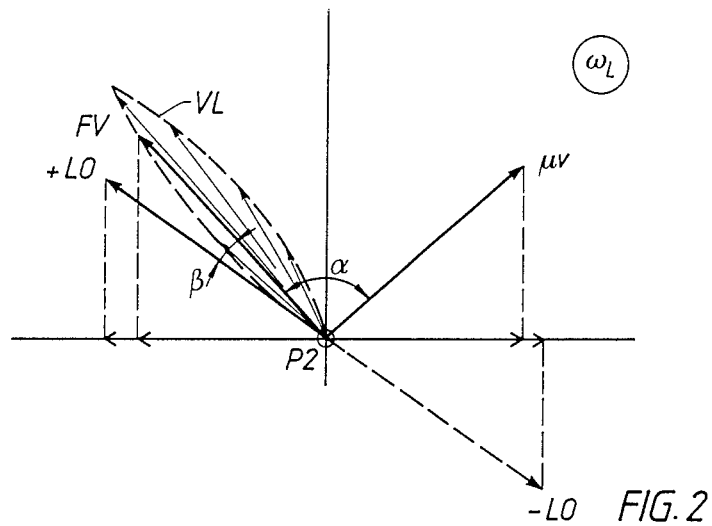
FIGS. 2 and 3 show vector diagrams for different frequencies.
Figure 3:
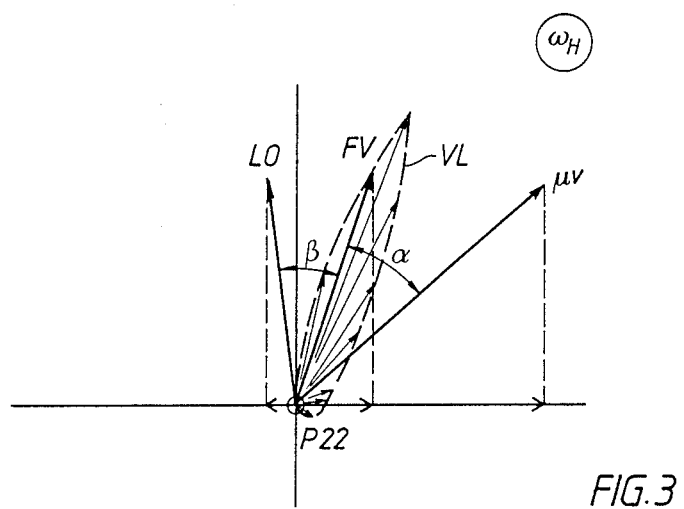

When using the term vector, this is often understood to include also a signal, for example an alternating voltage, the phase position of which represents the direction of the vector and the amplitude of which corresponds to the magnitude of the vector. In FIGS. 2 and 3 the socalled vector lobes (VL) have been indicated by dashed lines. These lobes indicate the limiting surface within which fault vectors of varying depth and vertical position are located. In the case of unusually large cracks, the length of the lobes may be greater than that shown.

It is easily realized that in addition to their magnetic vector, oxide scales also contain an LO-vector part because of their thickness. Therefore, oxide scales appear somewhat indefinitely in the impedance diagram. Howver, tests carried out in practice shown that the combined vector direction of oxide scales differs from surface cracks at higher frequencies, whereas at lower frequencies cracks do exist which are somewhat more difficult to phase-discriminate from certain types of oxide scale.

Although much of the impedance diagram according to FIG. 1 is known to the person skilled in the art, as far as I know no-one has attempted at or succeeded in drawing the conclusions which form the basis of the present invention. A probable explanation of this may be that magnetic permeability, as opposed to the electrical conductivity, is of no major interest to, for example, an end user of steel ingots such as slabs and the like, but has only been a problem for users of equipment for eddy current testing.

From FIG. 3 it is clear that the lower right-hand part of the vector lobe VL intersects the $\mu$-vector, $\mu V$. This part of the vector lobe usually represents cracks located somewhat deeper in the material, i.e. cracks not open to the surface. The consequence of this is that at higher frequencies there are cracks whose direction in the impedance diagram coincides with the $\mu$-direction. In other words, FV and $\mu V$ cannot be separated in a reliable manner merely by using phase discrimination at higher frequencies. On the other hand, at a suitably selected low frequency, as shown in FIG. 2, separating VL from $\mu V$, and inversely, does not present any problem, as in this case no intersection occurs. As far as is known, this fact has not been made use of by anyone in order to increase the reliability in crack detection, as described in the present application.

As a first step towards a reliable separation of the $\mu$-vector from the other vectors, a suitable, often low, frequency is chosen which provides a complete separation of $\mu V$ from FV. As a second step, for example, the lift-off (LO) vector is suppressed. It is to be noted here that LO may change polarity (see the $-LO$ dashed line in FIG. 2). Therefore, if, as indicated in FIG. 2, detection is carried out in a direction which is horizontal, the respective vector projection on the horizontal line will be approximately the same for $\mu V$ and $-LO$, which means that it is difficult, if not impossible, in this way to separate $\mu V$ from $-LO$. On the other hand, as can be seen in FIG. 2, at $\omega_L$ horizontal projections of FV and $\mu V$ can be separated from each other without difficulty since the projections of FV and $\mu V$ have different signs and can easily be distinguished one from the other by electronic means. At a sufficiently low frequency where the angle $\alpha$ or the sum of the angles $\alpha$ and $\beta$ is of the order of magnitude of 90°, it is possible relatively efficiently to suppress the LO-influence by detecting the vectors largely perpendicular to the LO-direction or the FV-direction, depending on which of these is the more disturbing for the $\mu$-vector separation.

In the case of normal surface cracks, the angle $\beta$ is often $< 18°$, which means that the fault vector FV is also suppressed relatively well when detecting perpendicular to the LO-direction. Because of the somewhat incomplete suppression of FV, however, it may be useful to improve the suppression via a filtering method. To this end, the fact that the frequency contents in the detected and rectified fault vector FV are higher than the frequency contents in the corresponding $\mu$-vector signal and the LO-vector signal, can be employed. The filters for the respective vector types are therefore tuned to different signal frequencies, whereby they can be more easily separated from each other. The reason for the different frequency contents is that cracks and possible magnetic portions of the test object have different shape and propagation. The transducer is thus likely to be located over a crack and over a magnetic portion for different periods of time.

Since the LO-signal also differs with respect to frequency from other signals or vectors, the LO-signal can also be separated or suppressed further via a filter method, if required. Another method of separating or suppressing both the LO-signals and oxide scale signals is via the type of transformation to which the present invention relates. In this case at least one LO-signal, or part thereof, of a different carrier frequency origin is employed in order to compensate, for example to balance away, the LO-vector. The same technique can also be employed for separation and suppression of FV-signals and so on. The invention includes both separate and combined solutions of the principles mentioned here.

In order for the vector transformation to operate satisfactorily, the relatively definite direction in the impedance diagram of the oxide scale vectors is a fundamental condition. It is also important that both the absolute direction and the direction relative to other vector types are different at different frequencies. The frequencies/carrier frequencies used may advantageously be, for example, 10 KHz (L) and 1 MHz (H), respectively.

To operate with a frequency ratio H/L>5 has in certain cases obvious advantages.

To prevent μ-vectors from being confused with fault vectors, it is desirable to use the detected presence of magnetic material for automatically blocking crack detection so that no false cracks are indicated. At the same time, some form of alarm can be given, for example automatically, in order to draw attention to the fact that crack detection has been temporarily blocked or is unreliable because of the presence of magnetic disturbances.

The presence of magnetic material can also be used as an indication that something is wrong in a continuous casting process, for example that excessive cooling is occurring in a continuous casting machine. When alarm is given indicating the presence of magnetic material, it is also possible—for example, automatically and temporarily —to activate devices for the removal of oxide scale and the like magnetic material from the test object.

In certain cases, it may be desirable that alarm is given when the permeability level exceeds a certain set threshold value. For that reason, the permeability signal should be largely constant within the LO operating range of the transducer. This can be achieved by signal processing, for example by amplifying, the μ-signal as a function of the LO-signal.

In those cases where the same transducer is used both for the detection of cracks and for detecting the presence of magnetic material, the following advantages, inter alia, may be obtained: The measurement takes place at the same time on the same surface part, so the measured values are the current ones and are related to each other. The permeability dependence of the crack detection is nearly exactly indicated because the same transducer is used for both measurements. The transducer arrangement is, of course, simpler and less expensive.

The above-mentioned U.S. Pat. No. 4,661,777 (Törnblom) relating to so-called dynamic transformation may, in certain cases, constitute a complement to the present invention, or vice versa, since the oxide scales because of their thickness often give rise to a disturbing lift-off vector. Particularly in the case of thick oxide scales occupying a large area, where the lift-off variations are considerable, it may be justified to make use of dynamic transformation.

In crack detection, some form of transducer manipulator is often used to move a transducer/sensor over, for example, a hot steel strand. The manipulator may be a so-called "whirligig" device, i.e. it moves the transducer/sensor along a rotary path superimposed on a slower scanning movement. The present invention includes those cases where separate transducers for detecting cracks and magnetically disturbing material are placed together on or in the same scanning arrangement, and this has several advantages. In this way, crack detectors can be blocked to an optimum extent, i.e. to precisely the right amount and for precisely the right period of time, since the information about the presence of magnetic material is both up-to-date and exact.

Figure 4:
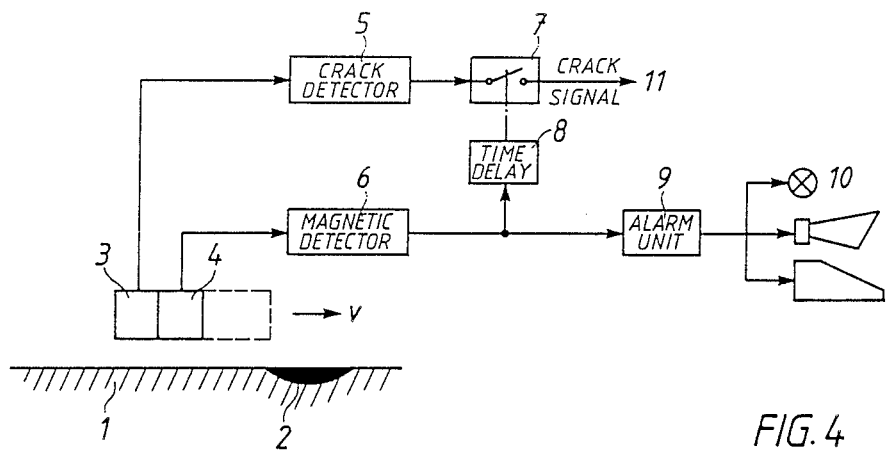
FIGS. 4 and 5 show block diagrams of equipment according to the invention.
Figure 5:
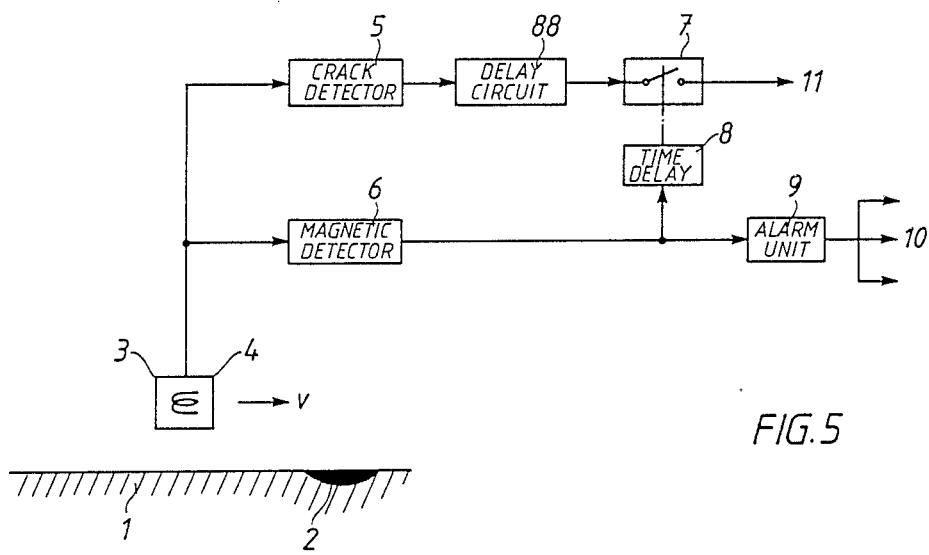

To illustrate how a crack detector and a magnetic or μ-detector can cooperate, two largely equivalent block diagrams are shown in FIGS. 4 and 5. Let it be assumed that the test object 1 contains a magnetic oxide scale flake 2. Two transducers 3 and 4 (which in FIG. 5 are shown as a common surface transducer coil) move over the surface of the test object 1 at a velocity v m/s in the direction of the arrow. The transducer/sensor consists of one crack transducer 3 and one magnetic sensor 4. The transducer/sensor is respectively connected to a crack detector 5 and a μdetector 6. The crack detector 5 is connected to a blocking circuit 7, from which crack signals can be obtained at an output 11. In FIG. 5 the crack signal also passes through a delay circuit 88. The output signal from the μ-detector 6 controls the blocking circuit 7 via a time delay unit 8, which may, for example, extend the control signal from the μ-detector 6 so as to obtain an optimum blocking. Different types of alarm signals 10 are given via an alarm unit 9. A particularly good arrangement is to locate the μ-transducer 4 immediately in front of the crack transducer 3 since in this way the crack detector 5 is blocked just before the crack transducer 3 reaches the disturbing region represented by the flake 2. The same end is achieved if, as shown in FIG. 5, the crack signal is delayed in the delay circuit 88, which may consist of an analog shift register or the like. This delay makes it possible for a false crack signal, which has arisen as a result of the flake 2 of magnetic material, to be blocked in a reliable manner by the signal from the μ-detector 6. Because of the delay in the circuit 88, the signal from the μ-detector 6 should be extended by the time delay unit 8, for example by a period somewhat longer than the delay time set by the delay circuit 88.

The alarm signals 10, about the presence of magnetic material, can be used to activate and/or control, for example, a separate device for the removal and/or elimination of the magnetic material and/or a suppression of its effects on, for example, the detection of cracks.

The invention thus embraces the use of a further device, for example controlled via an alarm signal 10, for eliminating completely or partially the magnetic properties of oxide scales and the like on, for example, hot test objects, by heating the oxide scales to a temperature corresponding to at least the Curie temperature of the oxide material, which renders the oxide scale largely non-magnetic. This heating can, for example, be achieved by heating up the oxide scales (e.g. using at least one gas burner or gas flame). Another way is to raise the temperature of the oxide scales by means of an inductive heating device. The heating device may advantageously be mounted on the scanning equipment adjacent to the transducer of the measuring and/or control device (e.g. as shown in dashed lines at 12 in FIG. 4). Such heating can be initiated. for example, when the μ-detector indicates that the oxide scales are magnetic or are tending to become magnetic. In this way, the heating can take place selectively in places here magnetic oxide scales and the like have become established. By locating the transducer/sensor for crack detection and μ-detection and the heating device 12 on the same movable support connected to, for example, a billet strand, for example on a cross-travel car, a financially attractive overall solution is obtained.

In summary, the invention comprises providing, for example, a conventional eddy-current based crack-detecting equipment, which is adapted to scan preferably non-magnetic test objects, with a device which detects—for example, advantageously via eddy current technique—the presence of disturbing magnetic material, for example relatively cold magnetic oxide scales, in and/or on the test object in order thus to monitor, for example, that disturbances (i.e. so-called "false" cracks) originating from the presence of magnetic material, are not confused with real cracks and similar harmful surface defects.

In order to avoid too large a proportion of the sensed surface becoming insensitive for crack detection because of excessive magnetic disturbances, the device can be provided with means (for example a heating device) to eliminate the magnetic properties of, for example, oxide scales.

It should be noted that the invention can be regarded as a further improvement of the invention defined in U.S. patent application 085,173 previously referred to, the present invention supplementing the earlier one insofar as the signal processing is concerned. This means that the invention can be realized as a separate device or it can be included as an integral part in another device, the task of which need not be to separate oxide scales and cracks from each other.

Figure 6:
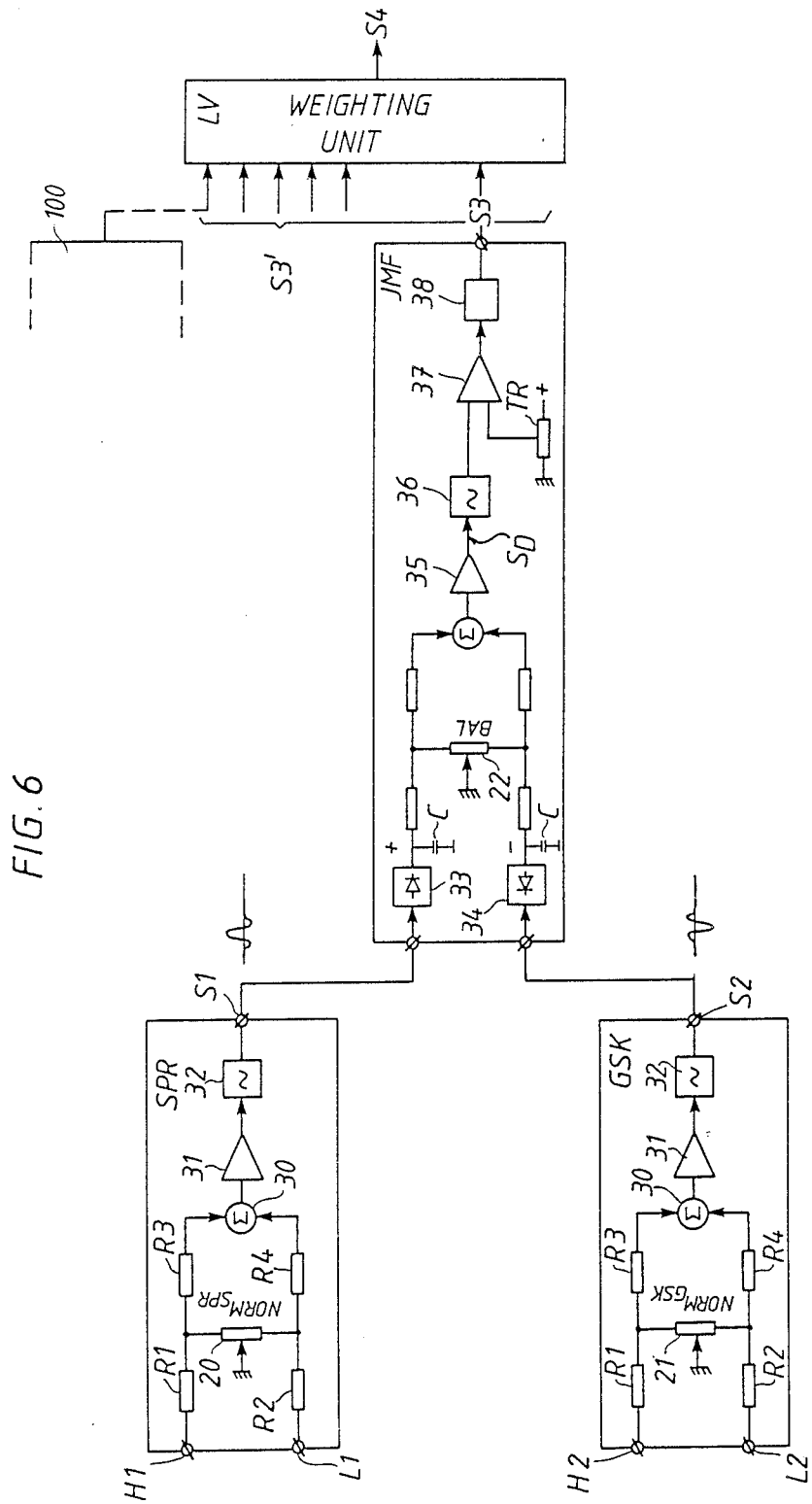
FIG. 6 shows a detail of FIGS. 4 and 5.

A detailed example of vector transformation, according to the present invention, in diagrammatic form is illustrated in FIG. 6. FIG. 6 can be regarded as a functional diagram of block 6 in FIGS. 4 and 5. Measurements in practice have shown that the cold oxide scales occur relatively stably in phase in the impedance diagram of the transducer; in other words, the oxide scale vectors have a relatively definite direction at the frequencies used. However, this direction varies between the frequencies themselves. In FIG. 6, input signals H1, L1, and H2, L2, respectively, consist of signals from, for example, phase-controlled rectifiers, so-called synchronous carrier frequency detectors. H1 and H2 originate from, for example, a high carrier frequency, for example 1 MHz, whereas L1 and L2 originate from, for example, a low carrier frequency, for example 20 KHz. H1, H2, L1 and L2 may be output signals from different detectors. For the sake of simplicity, it is assumed in the following that H1=H2 and L1=L2, which, however, is to be seen as one of many possible alternatives. H1=H2 and L1=L2, despite its simplicity, functions very well in practice.

FIG. 6 is divided into three functional units, namely a crack detection channel (SPR), an oxide scale detection channel (GSK) and a comparison channel (JMF). The task of the SPR unit is to generate a signal S1 and to suppress the effect of Lift-Off (LO) and signals arising from minor surface irregularities (often referred to as oscillation marks (OSCM)). The task of the GSK unit is to generate a signal S2. The task of the JMF unit is to compare the signals S1 and S2 with one another. An output signal S3 from the JMF unit is employed, for example, to block the crack detector unit in the presence of so-called false crack signals caused by oxide scales. The term "block" is to be construed in a broad manner and includes, for example, the meanings of "bar", "damp", "separate" or "short-circuit". It would, however, be possible to combine several signals of the same type as S3 into superordinate condition complexes, whereby it is of course, possible to carry out, for example, advanced signal separations or the like by using several S3-signals as digital input signals to one or more digital condition networks. In other words, FIG. 6. can be regarded as a building block, from which, by multiplying and combining more complex structures or networks can be built. By detecting the carrier frequency signals, as indicated in FIG. 6, so that the H- and L-signals assume different polarity, these can be weighted relative to each other by means of NORM-potentiometers 20 (NORM$_{SPR}$) and 21 (NOR$_{GSK}$), respectively. By grounding the center slide of the potentiometers 20, 21, as shown in FIG. 6, the respective transformation block can be normalized which significantly simplifies signal processing. The same is true of the balancing potentiometer 22 in unit JMF. For the SPR unit a position of potentiometer 20 must be chosen which gives a minimum output signal S1 for LO and OSCM. For the GSK unit, in a similar manner, a position of potentiometer 21 must be chosen which gives a minimum output signal S2 for oxide scale (GSK). The SPR and GSK units are to be regarded as separate, simple transformation blocks, usually utilizing different potentiometer settings to suppress the one or more variables requiring suppression. By thereafter combining several units, the number of suppressed variables can, of course, be increased in spite of the fact that the method for setting for each does not become more difficult. The optimum setting for the respective variable, of course, normally takes place by means of a setting of the separate potentiometer.

It is also worth noting that the respective units may otherwise advantageously be identically constructed. The units may also suitably be designated subtransformation complexes or the like. In practice, sometimes, signals from one unit are utilized in another unit. The important thing, however, is that the signals S1 and S2 originate from at least partially different normalizations in the two units generating them.

By the simple circuit solution, in which a resistance network R1, R2, R3, R4, a summer 30 and the potentiometer 20 constitute the weighting portion together with an amplifier 31 and a filter 32, the signals which are to be minimized can thus be suppressed individually by their separate normalization settings. This, of course, facilitates the signal processing.

Figure 7:
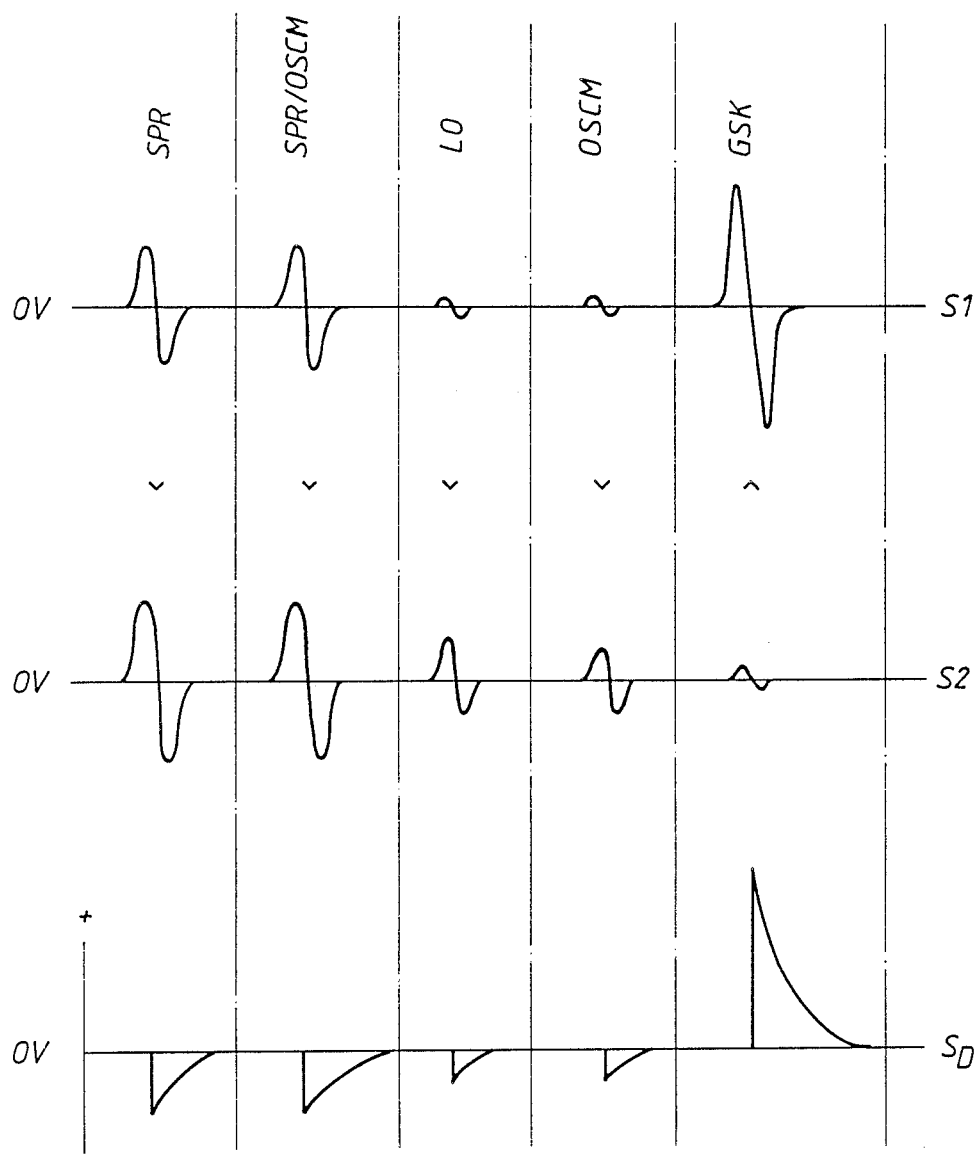
FIG. 7 illustrates different signals than can arise with the equipment of FIGS. 4 and 5.

By using the same input signals to the transformation units (H1=H2 and L1=L2) and normalizing the units for suppression of OSCM and of cold GSK, it is often adequate to use only two input signals. This, in combination with the above, forms the basis of a very simple setting. FIG. 7 shows how the different signals S1, S2 and S$_D$, because of the different NORM- and BAL-settings, vary in amplitude and shape depending on their origin, the phenomenon causing each signal being marked at the top of each column of S1, S2 and S$_D$ signals. The S1-signal exhibits a low amplitude for LO and OSCM whereas the S2-signal in a corresponding manner exhibits a low amplitude for GSK. The arrow heads between the S1- and S2-signals point to the larger signal for each respective phenomenon. As will be clear, the direction of the arrow head for GSK differs from the other four, which is important to note.

The task of the JMF-block in FIG. 6 is to compare the signals S1 and S2 with each other. By rectifying S1 and S2 via rectifiers 33 and 34, two signals of different polarity are obtained independently of whether S1 and S2 have an inverted appearance, as is shown in FIG. 6, or otherwise differ in shape. In other words, the full-wave rectification has an equalizing effect on the curve shapes of S1 and S2. If the rectifiers 33 and 34 are provided with capacitors C on their outputs, the equalizing effect will be further improved. A resistance network and summer (similar to those used in units SPR and GSK) feeds an amplifier 35, the output S$_D$ of which is fed to a filter 36. In FIG. 7 the S$_D$-signals are shown with a discharge curve shape, which is due to the capacitors C. The signals S1 and S2 can be weighted relative to each other by way of the balancing potentiometer 22, which can be seen as a superordinate normalization. By selecting a suitable setting for the potentiometer 22, the appearances of the $S_D$-signals obtained will be as shown in FIG. 7. As will be clear from FIG. 7, the signal from an area of oxide scale (GSK) has a positive polarity whereas the other input parameters/quantities each give rise to a negative polarity $S_D$ signal.

The consequence of the above is that, after character generation, weighting and summing of the signals S1 and S2 via, inter alia, the amplifier 35, the filter 36, and a suitable threshold voltage (TR) on an amplifier 37, it is possible to separate the oxide scale signals (GSK) from the other signals. In the block 38, the signal from the amplifier 37, for example, is digitized in order to impart a suitable shape and level to the output S3-signal. Thereafter, the S3-signal may, for example, be used for controlling/blocking the crack detection unit, by blocking the signal path or by, for example, resetting an error code register, and the like. The superordinate S4-signal outputting from a weighting unit (LV) can be used in a corresponding manner.

In those cases where it is desired to suppress several variables/quantities, it may be justified to extend the number of transformation complexes and a further one is partially shown at 100 in FIG. 6. Several S3-signals, S3', are then obtained, as is indicated in FIG. 6. These S3'-signals constitute input signals to the weighting unit, LV, which, for example, comprises logic conditions, i.e. a type of superordinate condition function. The output signal S4 from LV can be looked upon as a more sophisticated control signal than the S3-signal. The weighting unit LV may incorporate everything from simple threshold conditions to advanced and complex logic conditions, comprising, for example, AND- and OR-function gates or comparators. In this way, the transformation function thus used and supplemented becomes special in nature and may, for example, be used in spite of the fact that the quantity being monitored (in this case oxide scales) varies in shape and dimension and is thus difficult to suppress in a conventional manner.

Successively—i.e. unit by unit—suppressing a variable with one potentiometer per variable and/or unit provides for a simplicity of signal processing which is superior to other known methods.

In a conventional suppression of unwanted phenomena by means of vector transformation, as described in the above-mentioned patents/applications, the starting-points are continuous linear functions which are then normally represented by analog voltages, and via weighting methods, the unwanted phenomenon is suppressed. In contrast to this, a method involving comparison and conditions is utilized to determine the type of phenomenon, for example whether the surface crack on the billet surface is a genuine or a false crack.

The condition-based separation described above can also be used for detecting and/or suppressing phenomenon other than oxide scales and magnetic material so that these other applications are also embraced by this invention.

Since the transformation includes some kind of conditions, the requirement for accuracy of setting up is often reduced, since in many cases it is sufficient to determine the polarity of the $S_D$-signal to determine the type of signal occurring, for example whether or not it is a question of an oxide scale (see FIG. 7). This can also be expressed as follows. Instead of aiming at a complete suppression of the unwanted analog signal, as in the case of conventional transformation, according to the present invention a comparison is carried out, for example of the amplitude, between two separate signals derived from different transformation settings.

The invention can be varied in many ways within the scope of the following claims.

What is claimed is:

1. A device for monitoring a test object for the presence of oxide scale and cracks, comprising:
   a sensor adapted to be moved relative to the surface of the test object for generating sensor output signals representative of the detection of cracks and oxide scale;
   a magnetic detector responsive to said sensor output signal for detecting the presence of at least said oxide scale and generating a first output signal in response thereto;
   a crack detector responsive to said sensor output signal for detecting the presence of cracks and generating a second output signal in response thereto; and
   means responsive to said first output signal for blocking said second output signal to prevent detection of false cracks.

2. A device as claimed in claim 1, further comprising means for delaying said first output signal to the blocking means.

3. A device as claimed in claim 2, further comprising means for delaying said second output signal to the blocking means.

4. A device as claimed in claim 1, further comprising means for heating the surface of the test object adjacent said sensor, and means responsive to said first output signal for activating said heating means.

5. A device as claimed in claim 1, further comprising means responsive to said first output signal to generate an alarm to indicate the presence of oxide scale.

6. A device as claimed in claim 1, wherein the test object is a hot billet having cold oxide scale and said magnetic detector detecting said cold oxide scale to prevent detection of said cold oxide scale.

7. A device according to claim 1, wherein said magnetic detector includes a crack detection channel for generating a signal SI upon the detection of a crack, an oxide scale detection channel for generating a signal S2 upon the detection of oxide scale; and said blocking means includes a comparison channel responsive to said signals S1 and S2 for producing a signal for blocking said crack detection channel from generating said signal SI to prevent detection of a false crack.

8. A device as claimed in claim 7, wherein said crack detection channel including means for respectively weighting a high frequency signal H1 and low frequency signal L1 for producing said signal S1, and said oxide scale detection channel including second means for respectively weighting a high frequency signal H2 and a low frequency signal L2 for producing said signal S2, and said comparison channel including third means for respectively weighting said signal S1 and signal S2 for producing the blocking signal.

9. A device as claimed in claim 7 wherein said signal H1 equals said signal H2 and said L1 equals said signal L2.

10. A device as claimed in claim 8, wherein said means for weighting including means for generating opposite polarity signals from said signals H1 and said signs L1 and means for normalizing said opposite polarity signals for generating said signal S1, and said second means for weighting including means for generating second opposite polarity signals from said signal H2 and said signal L2, and second means for normalizing said second opposite polarity signals for generating said signal S2, and wherein said means for normalizing and said second means for normalizing have at least partially different normalizing functions.

11. A device as claimed in claim 9, wherein said third means for weighting includes means for generating third opposite polarity signals from said signal S1 and said signal S2, and means for balancing said second and third opposite polarity signals.

12. A device as claimed in 1, wherein said magnetic detector is located relative to said crack such that when said sensor is moved relative to the surface of the test object, said magnetic detector will generate a first output signal prior to said crack detector generating a second output signal.

13. A device as claimed in claim 12, wherein said means responsive to said first output signal for blocking said second output signal will block the generation of said second output signal by said crack detector.

* * * * *